(12) United States Patent
Farrell

(10) Patent No.: US 7,029,711 B2
(45) Date of Patent: Apr. 18, 2006

(54) MIXTURE OF AND METHOD OF MAKING A TRANCUTANEOUS PAIN RELIEF COMPOSITION

(76) Inventor: Shannon Lynn Farrell, 625 Espalande #33, Redondo Beach, CA (US) 90277

( * ) Notice: Subject to any disclaimer, the term of this patent is extended or adjusted under 35 U.S.C. 154(b) by 293 days.

(21) Appl. No.: 10/731,938

(22) Filed: Dec. 9, 2003

(65) Prior Publication Data
US 2005/0123619 A1 Jun. 9, 2005

(51) Int. Cl.
*A61K 35/78* (2006.01)
*A61K 35/12* (2006.01)

(52) U.S. Cl. .................. 424/725; 424/727; 424/736; 424/747; 424/522; 514/817

(58) Field of Classification Search .............. None
See application file for complete search history.

(56) References Cited

U.S. PATENT DOCUMENTS

| | | | |
|---|---|---|---|
| 5,178,879 A | 1/1993 | Adekunle et al. | |
| 5,288,491 A | 2/1994 | Moniz | |
| 5,560,910 A | 10/1996 | Crandall | |
| 5,698,227 A * | 12/1997 | Rivlin | 424/522 |
| 6,579,543 B1 * | 6/2003 | McClung | 424/728 |
| 6,756,064 B1 * | 6/2004 | Carrol | 424/742 |
| 2001/0033838 A1 * | 10/2001 | Farmer | 424/115 |

* cited by examiner

*Primary Examiner*—Christopher R. Tate
(74) *Attorney, Agent, or Firm*—James E. Parris

(57) ABSTRACT

A transcutaneous pain relief composition for applying to the skin, comprising a mixture of dimethyl sulfoxide, stearic acid, emulsifying wax, glycerine, emu oil, sal butter, glucosamine, coconut oil, white beeswax, active calendula oil, slippery elm oil, Chamomile oil, arnica Oil, valenrian oil, peppermint oil, grapefruit seed extract, lavender oil and distilled water is disclosed.

21 Claims, No Drawings

MIXTURE OF AND METHOD OF MAKING A TRANCUTANEOUS PAIN RELIEF COMPOSITION

FIELD OF THE INVENTION

The invention relates to transcutaneous pain relief compositions for applying on the skin to alleviate subcutaneous discomfort associated with muscle strain or ostioarthritis and to promote tissue healing.

BACKGROUND OF THE INVENTION

Compounds for topical pain relief have had widespread use. These compounds may provide pain relief in some circumstances when applied topically, however many products used to relieve pain only offer temporary relief and do not promote healing. Further, many topical pain relief compounds include camphor and/or capsaicin are known to cause skin irritation and considered malodorous. Capsicum is an oleoresin obtained by extracting cayenne pepper with ether. It has been used for many years in compositions intended for pain relief yet having undesirable skin irritants.

Patients having injured joints or damaged soft tissues generally do not benefit from these compounds, where they promote temporary pain relief but do little for tissue healing. Specifically, these compounds are ineffective transcutaneous carriers and do not transport tissue healing compounds past the skin to affected joint and soft tissue regions.

In other compounds using capsicum as a pain relief, n-decylmethyl sulfoxide is used as a transcutaneous carrier, see for example U.S. Pat. No. 5,560,910 (Crandall, W. T., Oct. 1, 1996) which teaches a topical anti-inflammatory composition containing bromelain, capsaicin and a penetrating agent selected from n-decylmethyl sulfoxide and lecithin organogel. Though these compounds having n-decylmethyl sulfoxide as a transcutaneous carrier are known to reduce pain, skin irritation and unpleasant odors are common to the use of capicum.

Other topical compositions for providing pain relief and anti-inflammatory action are known in the art, for example, U.S. Pat. No. 5,178,879 (Adekunle, M. et al., Jan. 12, 1993) discloses a topical pain relief gel containing capsaicin, water, alcohol and a carboxypolymethylene emulsifier.

U.S. Pat. No. 5,288,491 (Moniz, H., Feb. 22, 1994) discloses a method for processing the noni (*Morinda citrifolia*) plant into powder for use in therapeutic compositions.

U.S. Pat. No. 5,560,910 (Crandall, W. T., Oct. 1, 1996) further discloses a topical anti-inflammatory composition containing bromelain, capsaicin and a penetrating agent selected from n-decylmethyl sulfoxide and lecithin organogel.

What is needed is a transcutaneous composition for application near a painful region to provide injured joint and soft tissues with elements that promote tissue healing, pain relief and muscle relaxation, and that is non-irritating to the skin, easily absorbed, fast acting and pleasant to smell.

DETAILED DESCRIPTION

The present invention comprises novel transcutaneous compositions for application near painful regions to provide injured joint and soft tissues with elements that promote tissue healing, pain relief and muscle relaxation while being non-irritating to the skin, and are easily absorbed, fast acting and pleasant to smell. The advantages of the present invention emanate from the novel composition of the ingredients described below.

In one preferred embodiment, dimethyl sulfoxide (DMSO), having concentration between 1% and 16% by weight of the final composition is combined with glucosamine sulfate, having concentration between 0.8% and 14% by weight of the final composition, wherein the combination is mixed at room temperature, between 60–75 degrees F., until the glucosamine sulfate is dissolved to form a first mixture.

DMSO is a simple chemical made from wood pulp that is an effective transdermal carrier having the desired attributes in the current invention of penetrating the skin and promoting healing of pockets of inflammation.

Glucosamine sulfate, an amino sugar, is an important constituent in the current invention, where it promotes the formation and repair of cartilage in joints, and more particularly promotes healing of soft tissues.

A second mixture having a pleasant smell and qualities that are healthful to the skin, and which acts as a base for the first mixture, is prepared by combining sal butter having concentration between 0.8% and 11% by weight of the final composition, white coconut oil having between 0.05% and 4.5% by weight of the final composition and glycerine having between 0.5% and 15% by weight of the final composition and heat to melting point, approximately 140–160 degrees F.

Sal Butter is obtained from the fruit of the sal tree. From the sal tree fruit, the butter is extracted and further processed and refined to obtain a light colored butter. Its useful qualities in the current invention include low odor and smooth texture, where it contains mostly fatty acids. Sal Butter is solid at room temperature, but melts readily on contact with the skin. Other sal butter aspects important to the current invention are the excellent emollient properties, softening effects and easily spreadable on the skin. Sal butter has exceptionally good oxidative stability due to very low content of polyunsaturated fatty acids, and prevents drying of skin and development of wrinkles, thus reducing degeneration of skin cells and promotes skin flexibility restoration.

Coconut oil promotes skin repair and protects skin from free radicals. The oil is absorbed into the skin and into the cell structure of the connective tissues, limiting the damage that excessive sun exposure can cause and aid in healing and repairing, as are desired results when using the current invention.

Glycerine is a colorless, odorless, syrupy, sweet liquid, obtained by the saponification of natural fats and oils. It is excellent for skin as it attracts and holds moisture to the skin. This combination of sal butter, coconut oil and glycerine provides for the current invention, a stable emulsion due to a uniform triglyceride composition with a high oxidative stability.

Add to the second mixture, emulsifying wax having between 0.6% and 15% by weight of the final composition, and white beeswax having between 1.0% and 5.0% by weight of the final composition and steraic acid in an amount between 0.8% and 14% by weight of the final composition, heat to the melting point between 150–170 degrees F.

Emulsifying wax provides excellent composition stability to the current invention, and is very easy to use. It is used to obtain the desired viscosity of the mixture and to keep water and oils combined. White bees wax is bleached yellow wax and is prepared from the honeycomb of the bee. These constituents provide inert, water-soluble, emulsifying material to the combination. Stearic acid serves as a softener for the mixture.

Add to the second mixture, distilled water having between 7.0% and 55% by weight of the total composition. The second mixture is blended at low speed between 1–25 Hz until there is no separation, and the heat is reduced to 110–130 degrees F.

Add the first mixture comprising DMSO and glucosamine sulfate to the second mixture comprising sal butter, white coconut oil, glycerine, emulsifying wax white beeswax, stearic acid and distilled water, then blend these constituents at low speed between 1–25 Hz, until there is no separation. Remove the combined mixture from heat.

Add to the combined mixture emu oil having between 1.0% and 10% by weight of the total composition, active calendula oil having between 0.05% and 5.0% by weight of the total composition, slippery elm oil having between 0.05% and 5.0% by weight of the total composition, chamomile oil having between 0.05% and 5.0% by weight of the total composition, arnica oil having between 0.01% and 5.0% by weight of the total composition, valenrian oil having between 0.01% and 5.0% by weight of the total composition, peppermint oil having between 0.05% and 5.0% by weight of the total composition, grapefruit seed extract having between 0.09% and 2.5% by weight of the total composition, lavender oil having between 0.05% and 3.5% by weight of the total composition. Blend entire mixture at medium speed, between 50–100 Hz, until the mixture cools to room temperature, approximately 60–75 degrees F., approximately 25–30 minutes. Then blend at high speed, between 150–300 Hz until mixture is stiffened to desired consistency, approximately 5–10 minutes.

Emu oil has natural anti-inflammatory, healing properties with a wide range of omega oils that are known to facilitate good health. Emu oil is used in the current invention for pain management, wound care and skin care.

Calendula oil from calendula flowers is a soothing, restorative oil, good for any type of skin, but especially suitable for dry skin. Calendula oil is a traditional Mediterranean skin care used to help preserve skin freshness, protect skin from over drying, sun-induced wrinkles and sun caused aging during summer time. When used regularly the oil imparts deep olive shine to the skin, helps protect skin from age related thinning and drying out.

Anti-aging properties of calendula oil are the desired attributes for the current invention and have a high content and diversity of carotenes, phytosterols, polyphenyls, and essential fatty acids.

Slippery elm oil is an excellent demulcent and emollient for use in the current invention. Slippery elm oil is extracted from the bark of the American elm. It is considered a valuable remedy in herbal practice, where the abundant mucilage it contains has wonderful strengthening and healing qualities. The poultice is used in cases of boils, abscesses, ulcers or burns.

Chamomile oil is used in the current invention to promote the forming of scar tissue and aid in healing wounds. It is very good for dry skin, especially when it is inflamed and sensitive and can reduce the redness of broken capillaries.

The current invention includes arnica oil to reduce discoloration and swelling of injuries such as bruised tissue, black and blue injuries, sprains and sore muscles. Arnica is pain relieving, counteracts inflammation and reduces swelling and discoloration.

Valerian oil possesses many qualities and has many uses. In the present invention valerian oil is used for its soothing qualities as an antispasmodic, sedative and used as a depressant of the central nervous system. Additionally it is a bactericide, which promotes hygiene to injured regions.

Peppermint oil has the desired qualities for the current invention of relaxation and pain-relief, where it is used for muscular pains, sprains and neuralgia.

Grapefruit seed extract is used in the current invention as a natural antibiotic, antiseptic, disinfectant and preservative. It is used to promote the healing of atypical skin conditions.

Lavender is used in the current invention as a natural antibiotic, antiseptic, anti-depressant, sedative and de-toxifier. It is able to aid healing and prevent scarring. Lavender reduces anxiety, stress and tension and therefore it is used for calming, soothing and relaxation.

In one embodiment of the current invention, the transcutaneous pain relief composition comprises concentrations prepared in any quantity by maintaining equivalent ratios:
8.30% dimethyl sulfoxide;
7.30% stearic acid;
5.20% emulsifying wax;
5.20% glycerine;
4.60% emu oil;
6.20% sal butter;
6.20% glucosamine sulfate;
2:10% coconut oil;
2.10% white beeswax;
1.90% active calendula oil;
1.90% slippery elm oil;
2.30% chamomile oil;
1.00% arnica oil;
1.00% valenrian oil;
2.50% peppermint oil;
1.00% grapefruit seed extract
1.90% lavender oil;
39.40% distilled water.

It should be obvious to anyone skilled in the art that varying concentrations and order of combination of the above ingredients will not detract from the spirit of the invention.

What is claimed is:

1. A transcutaneous pain relief composition for applying to the skin, comprising effective amounts of a mixture of:
dimethyl sulfoxide;
stearic acid;
emulsifying wax;
glycerine;
emu oil;
sal butter;
glucosamine;
coconut oil;
white beeswax;
active calendula oil;
slippery elm oil;
chamomile oil;
arnica oil;
valerian oil;
peppermint oil;
grapefruit seed extract;
lavender oil;
distilled water.

2. The transcutaneous pain relief composition of claim 1, comprising the following components, prepared in any quantity by maintaining equivalent ratios:

| | |
|---|---|
| dimethyl sulfoxide | 8.30% |
| stearic acid | 7.30% |
| emulsifying wax | 5.20% |
| glycerine | 5.20% |
| emu oil | 4.60% |
| sal butter | 6.20% |
| glucosamine sulfate | 6.20% |
| coconut oil | 2.10% |
| white beeswax | 2.10% |
| active calendula oil | 1.90% |
| slippery elm oil | 1.90% |
| chamomile oil | 2.30% |
| arnica oil | 1.00% |
| valerian oil | 1.00% |
| peppermint oil | 2.50% |
| grapefruit seed extract | 1.00% |
| lavender oil | 1.90% |
| distilled water | 39.40% | wherein the amounts of any of said components may vary by plus or minus up to 10%.

3. The transcutaneous pain relief composition of claim 1, wherein the effective range of said dimethyl sulfoxide is between 1% and 16% by weight of said composition.

4. The transcutaneous pain relief composition of claim 1, wherein the effective range of said steraic acid is between 0.8% and 14% by weight of said composition.

5. The transcutaneous pain relief composition of claim 1, wherein the effective range of said emulsifying wax is between 0.6% and 15% by weight of said composition.

6. The transcutaneous pain relief composition of claim 1, wherein the effective range of said glycerine is between 0.5% and 15% by weight of said composition.

7. The transcutaneous pain relief composition of claim 1, wherein the effective range of said emu oil is between 1.0% and 10% by weight of said composition.

8. The transcutaneous pain relief composition of claim 1, wherein the effective range of said sal butter is between 0.8% and 11% by weight of said composition.

9. The transcutaneous pain relief composition of claim 1, wherein the effective range of said glucosamine sulfate is between 0.8% and 14% by weight of said composition.

10. The transcutaneous pain relief composition of claim 1, wherein the effective range of said coconut oil is between 0.05% and 4.5% by weight of said composition.

11. The transcutaneous pain relief composition of claim 1, wherein the effective range of said white beeswax is between 1.0% and 5.0% by weight of said composition.

12. The transcutaneous pain relief composition of claim 1, wherein the effective range of said active calendula Oil is between 0.05% and 5.0% by weight of said composition.

13. The transcutaneous pain relief composition of claim 1, wherein the effective range of said slippery elm oil is between 0.05% and 5.0% by weight of said composition.

14. The transcutaneous pain relief composition of claim 1, wherein the effective range of said chamomile oil is between 0.05% and 5.0% by weight of said composition.

15. The transcutaneous pain relief composition of claim 1, wherein the effective range of said arnica oil is between 0.01% and 5.0% by weight of said composition.

16. The transcutaneous pain relief composition of claim 1, wherein the effective range of said valenrian oil is between 0.01% and 5.0% by weight of said composition.

17. The transcutaneous pain relief composition of claim 1, wherein the effective range of said peppermint oil is between 0.05% and 5.0% by weight of said composition.

18. The transcutaneous pain relief composition of claim 1, wherein the effective range of said grapefruit seed extract is between 0.09% and 2.5% by weight of said composition.

19. The transcutaneous pain relief composition of claim 1, wherein the effective range of said lavender oil is between 0.05% and 3.5% by weight of said composition.

20. The transcutaneous pain relief composition of claim 1, wherein the effective range of said distilled water is between 7.0% and 55% by weight of said composition.

21. A method of making a transcutaneous pain relief composition comprising the steps of:

combining dimethyl sulfoxide (DMSO), having concentration between 1% and 16% by weight of the final composition with glucosamine sulfate, having concentration between 0.8% and 14% by weight of the final composition, wherein the combination is mixed at room temperature, between 60–75 degrees F., until the glucosamine sulfate is dissolved to form a first mixture;

preparing a second mixture as a carrier for said first mixture by combining the ingredients sal butter having concentration between 0.8% and 11% by weight of the final composition, white coconut oil having between 0.05% and 4.5% by weight of the final composition, and glycerine having between 0.5% and 15% by weight of the final composition;

heating said second mixture to melting point, approximately 140–160 degrees F.;

adding to said second mixture, emulsifying wax having between 0.6% and 15% by weight of the final composition, white beeswax having between 1.0% and 5.0% by weight of the final composition and steraic acid in an amount between 0.8% and 14% by weight of the final composition;

heating said second mixture to the melting point between 150–170 degrees F.

adding to said second mixture distilled water having between 7.0% and 55% by weight of the total composition;

blending said second mixture at low speed between 1–25 Hz until there is no separation;

reducing heat to 110–130 degrees F.;

adding said first mixture to said second mixture to create a combined mixture;

blending said combined mixture at low speed between 1–25 Hz, until there is no separation;

removing said combined mixture from heat;

adding to said combined mixture emu oil having between 1.0% and 10% by weight of the total composition, active calendula oil having between 0.05% and 5.0% by weight of the total composition, slippery elm oil having between 0.05% and 5.0% by weight of the total composition, chamomile oil having between 0.05% and 5.0% by weight of the total composition, arnica oil having between 0.01% and 5.0% by weight of the total composition, valerian oil having between 0.01% and 5.0% by weight of the total composition, peppermint oil having between 0.05% and 5.0% by weight of the total composition, grapefruit seed extract having between 0.09% and 2.5% by weight of the total composition, lavender oil having between 0.05% and 3.5% by weight of the total composition;

blending said combined mixture at medium speed, between 50–100 Hz, until said combined mixture cools to room temperature, 60–75 degrees F.;

blending said combined mixture at high speed, between 150–300 Hz, until said combined mixture is stiffened to desired consistency.

* * * * *